United States Patent [19]

Mori

[11] Patent Number: 4,782,818
[45] Date of Patent: Nov. 8, 1988

[54] ENDOSCOPE FOR GUIDING RADIATION LIGHT RAYS FOR USE IN MEDICAL TREATMENT

[76] Inventor: Kei Mori, 3-16-3-501, Kaminoge, Setagaya-ku, Tokyo, Japan

[21] Appl. No.: 914,896

[22] Filed: Oct. 3, 1986

[30] Foreign Application Priority Data

Jan. 23, 1986 [JP] Japan ............................. 61-12498

[51] Int. Cl.⁴ .............................................. A61B 1/06
[52] U.S. Cl. ......................................... 128/6; 128/398
[58] Field of Search ...................... 128/4, 6, 395, 396, 128/397, 398

[56] References Cited

U.S. PATENT DOCUMENTS

| 2,843,112 | 7/1958 | Miller | 128/6 |
| 3,456,641 | 7/1969 | Yokota et al. | 128/397 X |
| 4,201,199 | 5/1980 | Smith | 128/6 X |

Primary Examiner—William H. Grieb
Attorney, Agent, or Firm—Jordan and Hamburg

[57] ABSTRACT

An endoscope or insertion tool for guiding radiation light rays for use in medical treatment is removably connected with a light rays emitting end portion of an optical conductor cable through which light rays corresponding to the visible light rays component of solar rays are transmitted. The endoscope comprises a transparent or semitransparent fine elongated tube having a closed tip end portion, the elongated tube having a light filter therein adjacent to the connecting portion to be connected with the optical conductor cable.

22 Claims, 2 Drawing Sheets

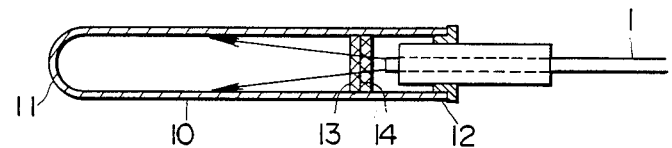
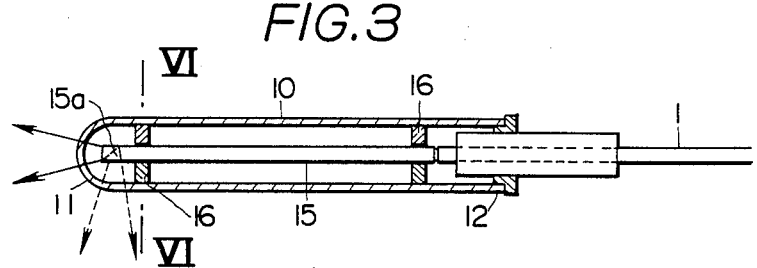
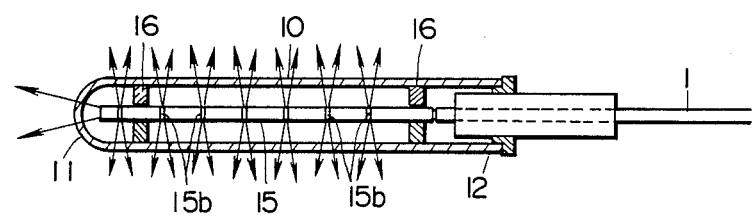
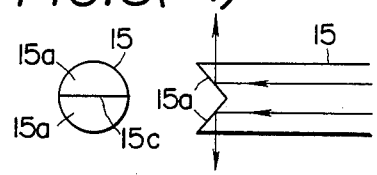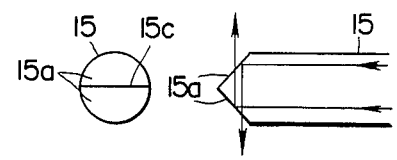
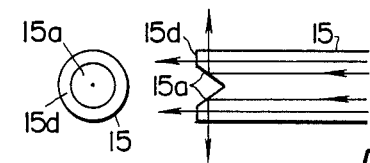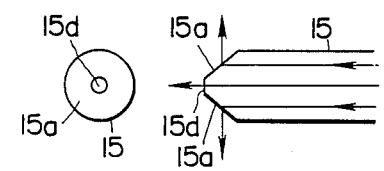
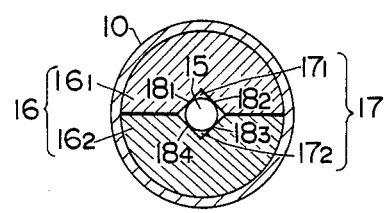

ENDOSCOPE FOR GUIDING RADIATION LIGHT RAYS FOR USE IN MEDICAL TREATMENT

BACKGROUND OF THE INVENTION

The present invention relates to an endoscope or insertion tool for guiding radiation light rays for use in medical treatment and preferable for radiating light rays such as solar rays, etc. effective for medically treating the inner surface of the interior of the mouth, ear, nose, throat, rectum, and so on.

In the recent years, a large number of persons suffer from incurable diseases such as arthritis, neuralgia and rheumatism, or in pain due to an injury or a bone fracture, or due to other diseases. Furthermore, any person cannot avoid aging of one's skin which progresses gradually from a comparatively young age. On the other hand, the present applicant has previously proposed to focus solar rays or artificial light rays by use of lenses or the like, to guide the same into an optical conductor, and to transmit those rays onto an optional desired place through the optical conductor. These solar rays or artificial light rays transmitted in such a way are employed for use in illumination or for other like purposes, for example, to cultivate plants, chlorella, or the like. In the process thereof, visible light rays not containing ultraviolet, infrared, etc. promote a living body reaction, and thereby the same promote the health of a person or prevent a person's skin from aging. Furthermore, these visible light rays noticeable effect recovery from arthritis, neuralgia, bedsores, rheumatism, burns, skin disease, injuries, bone fractures, or the like, and also stop the pain of these afore-mentioned diseases. Such effects obtained by use of the device according to the present invention have already been found by the present applicant.

And further, in consideration of the actual situation as mentioned above, the present applicant has previously proposed a light rays radiation device for medical treatment capable of performing various medical treatment or beauty treatment or promotion of a person's health by radiating the light rays corresponding to the visible light rays component of solar rays and not containing harmful components such as ultraviolet, infrared, etc.

A light rays radiation device for medical treatment which has been previously proposed by the present applicant comprises an optical conductor cable and a semitransparent cylindrical hood member. Solar rays or artificial light rays are guided into the optical conductor cable from an end portion thereof, and the guided light rays are transmitted therethrough. Light rays (white-colored light rays) corresponding to the visible light rays component of solar rays are transmitted through the optical conductor cable in such a manner as proposed previously by the present applicant in various ways. A semitransparent cylindrical hood member is installed at the light rays emitting end portion of the optical conductor cable. At the time of medical treatment, a patient is laid on a chair and the light rays of the visible light rays component are transmitted through the optical conductor cable in such a manner as mentioned before and are radiated onto the diseased part of the patient.

As mentioned above, the light rays radiated onto the diseased part of the patient are the light rays corresponding to the visible light rays component of solar rays containing therein neither ultraviolet nor infrared. Thereby, medical treatment can be done without suffering from any deleterious influence due to ultraviolet and infrared rays. However, the aforementioned light rays radiation device for medical treatment is employed mainly for the purpose of radiating the light rays onto the surface of the the skin of a patient. Consequently, in the case of curing the diseased part on the inner surface of the mouth interior, ear, nose, throat, rectum, etc., it is impossible to guide the light rays onto the diseased part, and therefore the effect of medical treatment cannot be sufficiently effected.

SUMMARY OF THE INVENTION

It is an object of the present invention to provide an endoscope or insertion tool for guiding radiation light rays for use in medical treatment.

It is another object of the present invention to provide an endoscope or tool which is preferable for inserting and radiating light rays onto the inner surface of the mouth, ear, nose, throat, rectum, and so on.

The above-mentioned features and other advantages of the present invention will be apparent from the following detailed description which goes with the accompanying drawings.

BRIEF DESCRIPTION OF THE DRAWINGS

FIG. 2 is a cross-sectional view for explaining embodiment of an endoscope or insertion tool for guiding radiation light rays for use in medical treatment according to the present invention;

FIG. 3 is a cross sectional view, similar to FIG. 2, of another embodiment;

FIG. 4 is a cross sectional view, similar to FIG. 2, of yet another embodiment;

FIGS. 5(A) through 5(D) are views showing, respectively, the shapes of the inclined surfaces at the tip end portion of the optical conductor 15 shown in FIG. 3 and FIG. 4; and FIG. 6 is a cross-sectional view of the support member 16 shown in FIGS. 3 and 4 taken along the line VI—VI in FIG. 3.

DESCRIPTION OF THE PREFERRED EMBODIMENTS

Figure 1:
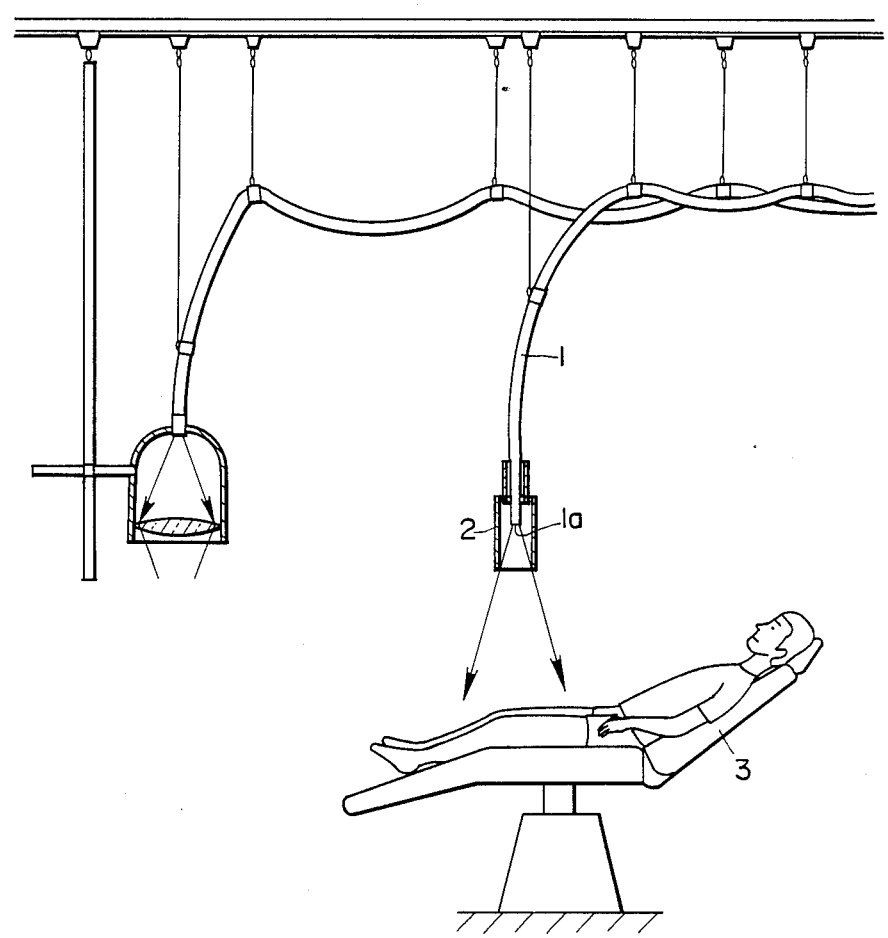
FIG. 1 is a construction view for explaining an embodiment of the light rays radiation device for medical treatment which has been previously proposed by the present applicant.

FIG. 1 is a construction view for explaining an embodiment of the light rays radiation device for medical treatment which has been previously proposed by the present applicant. In FIG. 1, 1 is an optical conductor cable. Solar rays or artificial light rays are guided into the optical conductor cable 1 from an end portion thereof not shown in FIG. 1, and the guided light rays are transmitted therethrough. Light rays (white-colored light rays) corresponding to the visible light rays component of solar rays are transmitted through the optical conductor cable 1 in such a manner as proposed previously by the present applicant in various ways.

In FIG. 1, 2 is a semitransparent cylindrical hood member installed at the light rays emitted end portion 1a of the optical conductor cable 1, and 3 is a chair for medical treatment. At the time of medical treatment, a patient is laid on the chair 3 and the light rays of the visible light rays component transmitted through the optical conductor cable 1 in such a manner as mentioned before are radiated onto the diseased part of the patient.

FIG. 2 is a cross-sectional view showing an embodiment of an endoscope or insertion tool for guiding radiation light rays for use in medical treatment according to the present invention. In FIG. 2, 10 is a fine elongated tube comprising a transparent or semitransparent member. One end portion 11 of the tube 10 is closed and another end portion 12 thereof is removably connected with the light rays emitting side of the optical conductor cable 1. The length and the diameter of the fine elongated tube are predetermined in accordance with the position for medical treatment to be performed, that is, the inner surface of the mouth interior, ear, nose, throat, rectum, and so on. At the time of performing medical treatment, one of the insertion tools which is most suitable for the medical treatment position is selected and connected with the optical conductor cable 1 for use in medical treatment.

In general, light rays suitable for medical treatment are white-colored light rays as mentioned before. It is possible to focus solar rays by use of the lens or the like and guide the light rays corresponding to the white-colored light rays component into the optical conductor cable 1. However, even on that occasion, the light rays comprising the components of light rays near infrared and light rays near ultraviolet are contained in the guided light rays to some degree. Occasionally, those light rays near infrared or ultraviolet exert an evil influence on the diseased part.

In FIG. 2, 13 is a filter for intercepting the light rays near infrared (or ultraviolet), and such deleterious influence due to the light rays near infrared (or ultraviolet) is removed by use of the filter 13. In addition to the filter 13, another filter 14 is superposingly installed on the filter 13 in order to further intercept the light rays near ultraviolet (or infrared). The fine elongated tube 10 thus intercepts the light rays near ultraviolet (or infrared) so that the tube 10 can cut off the light rays near infrared and ultraviolet.

FIG. 3 is a cross-sectional view for explaining another embodiment of an endoscope or insertion tool for guiding radiation light rays for use in medical treatment according to the present invention. In this embodiment, an optical conductor 15 is coaxially supported by use of a support member 16 in the fine elongated tube 10. When the tube 10 is connected with the optical conductor cable 1, the axis of the optical conductor 15 coincides with that of the optical conductor cable 1. The light rays emitted from the end portion of the optical conductor cable 1 are transmitted through the optical conductor cable 15 and radiated from the tip end portion of the fine elongated tube 10.

Furthermore, if the tip end portion of the optical conductor 15 is cut to form an inclined surface in relation to the axis line of the optical conductor 15 as shown by the broken line 15a in FIG. 3, the light rays are radiated from the tip end portion of the optical conductor 15 in a direction deflected from the axis of the optical conductor 15. For instance, the light rays can be radiated onto the upper side, lower side, or lateral side in the mouth interior.

FIG. 4 is a cross-sectional construction view of still another embodiment of an endoscope or insertion tool for guiding radiation light rays for use in medical treatment according to the present invention. In this embodiment, as already proposed in various ways by the present applicant, for instance, a cut groove is formed on the circumferential surface of the optical conductor 15 as in the embodiment shown in FIG. 3 or substance of a refractive index larger than that of the optical conductor is painted thereon, in order to provide a light rays emitting portion 15b, so that the light rays emitted almost uniformly over the entire area along the axial direction of the fine elongated tube 10. In such a manner, for instance, the insertion tool can be preferably employed for insertion into the rectum, etc. and radiating the light rays onto the overall inner surface of the rectum.

FIGS. 5(A) through 5(D) are, respectively, enlarged views showing modifications of the inclined surface 15a at the tip end portion of the optical conductor 15 shown in FIGS. 3 and 4. FIGS. 5(A) and 5(B) show modifications in which inclined surfaces 5a, 15a are formed symmetrically in relation to the plane 15c containing the center of the optical conductor 15 so as to radiate the light rays in two directions opposite to each other at the tip end portion of the optical conductor 15. The inclination angle of the inclined surface 15a is optional. The inclined surface 15a may be formed leaving partly a surface perpendicular to the axis of the optical conductor 15 so as to direct a part of the light rays in a straight line.

In FIGS. 5 (C) and 5 (D), the tip end portion of the optical conductor 15 is formed in a conical shape to provide an inclined surface 15a so that the light rays transmitted through the optical conductor 15 are radiated in an entire circumferential direction at the tip end portion of the optical conductor 15. The inclined surface 15a may be formed leaving partly a surface 15d perpendicular to the axis of the optical conductor 15 at the tip end portion thereof so as to radiate a part of the light rays transmitted through the optical conductor 15 in a direction along the axis of the optical conductor 15.

FIG. 6 is a cross-sectional view of the support member 16 shown in FIG. 3 taken along the line VI—VI in FIG. 3 . The support member 16 is divided into two semicircular members $16_1$ and $16_2$ having a diameter equal to the inner diameter of the fine elongated tube 10 as shown in FIG. 6. Since both of the semicircular members $16_1$ and $16_2$ have notches $17_1$ and $17_2$, respectively, when both members are combined into one, a hole 17 of square cross-section having a side approximately equal to the diameter of the optical conductor 15 is formed in the center thereof.

As a consequence thereof, the optical conductor 15 is clippingly supported in the hole 17, and thereby the optical conductor 15 and the support member 16 come into contact with each other at the four points $18_1$ through $18_4$. Both of them are joined at those points by use of adhesive such as optical paste or the like in order to combine them into one. Since the joined portions come into contact with each other at the respective points, there is no fear that the light rays will leak from the joined portions.

After joining the optical conductor 15 and the support member 16 as mentioned above, the joined combination is inserted into the fine elongated tube 10 and, for instance, the outer circumferential portion of the support member 16 nearest to the optical conductor cable 1 is joined to the fine elongated tube 10 by use of optical paste or the like. In such a manner as mentioned heretofore, the construction of the endoscope or insertion tools as shown in FIG. 3 and FIG. 4 can be easily obtained.

As is apparent from the foregoing description, according to the present invention, it may be possible to provide an endoscope or insertion tool for guiding radiation light rays for use in medical treatment which is preferable for performing medical treatment by inserting the endoscope or insertion tool and radiating the light rays onto the inner surface of the interior of the mouth, ear, nose, throat, rectum, and so on.

I claim:

1. An endoscope for guiding radiation light rays for use in medical treatment comprising an elongated optical conductor for transmitting light rays corresponding to the visible light rays component of solar rays, said conductor having a longitudinal end portion, an elongated tube means having one longitudinal end which is closed, the other longitudinal end of said tube means having receiving means for receiving said longitudinal end portion of said conductor such that said longitudinal end portion of said conductor extends into said tube means, filter means in said tube means, said longitudinal end portion of said conductor having a terminating end disposed between said filter means and said receiving means, said tube means having an elongated longitudinally extending tube section of constant inner and outer diameters extending between said closed end and said receiving means, said inner diameter of said elongated tube section being greater than the outer diameter of said conductor so as to form an annular space between said inner diameter of said elongated tube and said conductor such that light rays transmitted by said conductor radiate from said terminating end of said conductor are transmitted in a generally axially and radially outward direction to pass through said filter means and onto said elongated tube section to thereby effect radiation of filtered light rays generally radially outwardly along the axial length of said elongated tube section.

2. An endoscope according to claim 1, wherein said filter means filter out ultraviolet rays.

3. An endoscope according to claim 1, wherein said filter means filter out infrared rays.

4. An endoscope according to claim 1, wherein said filter means filter out ultraviolet rays and infrared rays.

5. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, and light rays discharging means on the circumference of said end portion of said conductor means for discharging light rays laterally along at least a part of the longitudinal length of said longitudinal end portion of said conductor means.

6. An endoscope according to claim 5, wherein said discharging means extends along the longitudinal length of said longitudinal end section of said conductor means.

7. An endoscope according to claim 6, wherein said discharging means are spaced along the longitudinal length of said conductor means.

8. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, and support means in said tube means for supporting said end portion of said conductor means such that the longitudinal axis of said conductor means is coincident with the longitudinal axis of said tube means, and inclined surface means on said longitudinal end portion of said conductor means for deflecting transmitted light rays laterally of the longitudinal axis of said conductor means, said inclined surface means comprising two inclined flat surfaces joined at a line of intersection which passes through the longitudinal axis of said conductor means and which extends perpendicular to the longitudinal axis of said conductor means.

9. An endoscope according to claim 4, wherein said inclined flat surfaces diverge outwardly from the longitudinal axis of said conductor means as the terminating end of the conductor means is approached.

10. An endoscope according to claim 8, wherein said inclined flat surfaces converge inwardly toward the longitudinal axis of said conductor means as the terminating end of said conductor means is approached.

11. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, and support means in said tube means for supporting said end portion of said conductor means such that the longitudinal axis of said conductor means is coincident with the longitudinal axis of said tube means, and inclined surface means on said longitudinal end portion of said conductor means for deflecting transmitted light rays laterally of the longitudinal axis of said conductor means, said inclined surface means comprising a concave conical surface coaxial with the longitudinal axis of said conductor means.

12. An endoscope according to claim 11, wherein said concave conical surface terminates at the terminating end of said conductor means along a terminating circle, said terminating circle being spaced radially inwardly of the outer circumference of said terminating end of said conductor means to define an annular portion on said terminating end which is perpendicular to the longitudinal axis of said conductor means.

13. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, and support means in said tube means for supporting said end portion of said conductor means such that the longitudinal axis of said conductor means is coincident with the longitudinal axis of said tube means, and inclined surface means on said longitudinal end portion of said conductor means for deflecting transmitted light rays laterally of the longitudinal axis of said conductor means. said inclined surface means comprising a convex conical surface coaxial with the longitudinal axis of said conductor means.

14. An endoscope according to claim 13, wherein said convex surface terminates at the terminating end of said conductor means to define a circular terminating end surface which is perpendicular to the longitudinal axis of said conductor means.

15. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, and support means in said tube means for supporting said end portion of said conductor means such that the longitudinal axis of said conductor means is coincident with the longitudinal axis of said tube means, said support means comprising two longitudinal spaced support parts, and inclined surface means on said longitudinal end portion of said conductor means for deflecting transmitted light rays laterally of the longitudinal axis of said conductor means.

16. An endoscope according to claim 15, wherein said longitudinal end portion of said conductor means has a terminating end and a tip portion juxtaposed to said terminating end, said inclined surface means comprising a cut inclined surface on said tip portion, said cut inclined surface being inclined relative to the longitudinal axis of said conductor means.

17. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, and support means in said tube means for supporting said end portion of said conductor means such that the longitudinal axis of said conductor means is coincident with the longitudinal axis of said tube means, said support means comprising two semi-circular support members which abut one another along a plane which contains the longitudinal axis of said conductor means, said semi-circular support members having a diameter equal to the inner diameter of said tube means, and inclined surface means on said longitudinal end portion of said conductor means for deflecting transmitted light rays laterally of the longitudinal axis of said conductor means.

18. An endoscope according to claim 17, wherein each of said support members has a notch which mates with one another to define a hole, said conductor means being received and supported in said hole.

19. An endoscope according to claim 18, wherein said hole is square and the length of any side of the square hole is substantially equal to the outer diameter of said conductor means.

20. An endoscope according to claim 18 further comprising optical paste means securing said optical conductor means in said hole.

21. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, said longitudinal end portion of said conductor means comprising a first conductor part and a second conductor part, each of said conductor parts having longitudinal end faces which contact one another such that light rays are transmitted between said first and second parts, said end faces being disposed in said tube means, and support means in said tube means for supporting said end portion of said conductor means such that the longitudinal axis of said conductor means is coincident with the longitudinal axis of said tube means, and inclined surface means on said longitudinal end portion of said conductor means for deflecting transmitted light rays laterally of the longitudinal axis of said conductor means.

22. An endoscope for guiding radiation light rays for use in medical treatment comprising an elongated optical conductor means for transmitting light rays corresponding to the visible light rays component of solar rays, said conductor means having a longitudinal end portion, an elongated tube means having one longitudinal end which is closed, the other longitudinal end of said tube means having receiving means for receiving said longitudinal end portion of said conductor means such that said longitudinal end portion of said conductor means extends into said tube means, said tube means having an inner diameter greater than the outer diameter of said conductor means, said longitudinal end portion of said conductor means comprising a first conductor part and a second conductor part, each of said conductor parts having longitudinal end faces which are juxtaposed to one another such that light rays are transmitted between said first and second parts, said end faces being disposed in said tube means, and support means in said tube means for supporting said end portion of said conductor means such that the longitudinal axis of said conductor means is coincident with the longitudinal axis of said tube means, and inclinded surface means on said longitudinal end portion of said conductor means for deflecting transmitted light rays laterally of the longitudinal axis of said conductor means.

* * * * *